United States Patent
Bis et al.

(10) Patent No.: US 6,493,571 B1
(45) Date of Patent: Dec. 10, 2002

(54) RAPID MAGNETIC RESONANCE IMAGING AND MAGNETIC RESONANCE ANGIOGRAPHY OF MULTIPLE ANATOMICAL TERRITORIES

(75) Inventors: Kostaki G. Bis, Bloomfield Hills, MI (US); Anil N. Shetty, Troy, MI (US)

(73) Assignee: William Beaumont Hospital, Royal Oak, MI (US)

(*) Notice: Subject to any disclaimer, the term of this patent is extended or adjusted under 35 U.S.C. 154(b) by 0 days.

(21) Appl. No.: 09/486,124

(22) PCT Filed: Apr. 10, 1998

(86) PCT No.: PCT/US98/07342
§ 371 (c)(1),
(2), (4) Date: Jun. 12, 2000

(87) PCT Pub. No.: WO98/46983
PCT Pub. Date: Oct. 22, 1998

Related U.S. Application Data

(60) Provisional application No. 60/043,899, filed on Apr. 11, 1997.

(51) Int. Cl.[7] ............................................... A61B 5/055
(52) U.S. Cl. ........................ 600/420; 600/421; 324/307; 324/309; 324/318; 5/601; 5/943
(58) Field of Search ................................. 600/410, 420, 600/415, 419, 421, 422; 324/306, 307, 309, 318; 5/600, 601

(56) References Cited

U.S. PATENT DOCUMENTS

| | | | |
|---|---|---|---|
| 4,686,692 A | | 8/1987 | DeMeester et al. |
| 4,727,328 A | * | 2/1988 | Carper et al. ............... 324/318 |
| 4,875,485 A | | 10/1989 | Matsutani |
| 5,361,763 A | | 11/1994 | Kao et al. |
| 5,363,844 A | | 11/1994 | Riederer et al. |
| 5,398,686 A | * | 3/1995 | Inone et al. ............. 128/653.2 |
| 5,423,315 A | | 6/1995 | Margosian et al. |
| 5,490,508 A | * | 2/1996 | Kato ....................... 128/653.5 |
| 5,562,094 A | | 10/1996 | Bonutti |
| 5,588,430 A | | 12/1996 | Bova et al. |
| 5,590,429 A | * | 1/1997 | Boomgaarden et al. ........ 5/600 |
| 5,657,757 A | | 8/1997 | Hurd et al. |
| 5,808,468 A | | 9/1998 | Bis et al. |
| 5,924,987 A | * | 7/1999 | Meaney et al. ............. 600/420 |
| 5,928,148 A | | 7/1999 | Wang et al. |
| 6,044,289 A | * | 3/2000 | Bonutti ..................... 600/415 |
| 6,052,476 A | * | 4/2000 | Qian et al. .................. 382/130 |
| 6,137,291 A | * | 10/2000 | Szumowski et al. ........ 324/318 |

* cited by examiner

Primary Examiner—Marvin M. Lateef
Assistant Examiner—Eleni Mantis Mercader
(74) Attorney, Agent, or Firm—Brinks Hofer Gilson & Lione

(57) ABSTRACT

A procedure and apparatus are provided which allow rapid positional change in the patient centering in order to facilitate the imaging of blood vessels in a series of different views. This procedure and apparatus can also facilitate the imaging of other tissues of the body at different spatial locations as well. The procedure and apparatus reduce the time required for obtaining the necessary images for a medical imaging examination using a single injection of an MRI or iodinated contrast agent.

10 Claims, 6 Drawing Sheets

RAPID MAGNETIC RESONANCE IMAGING AND MAGNETIC RESONANCE ANGIOGRAPHY OF MULTIPLE ANATOMICAL TERRITORIES

This application claims the benefit of Provisional Application No. 60/043,899 filed Apr. 11, 1997.

BACKGROUND OF THE INVENTION

1. Field of the Invention

The present invention relates generally to medical diagnostic procedures. More particularly the invention relates to use of a kinematic imaging table for rapid positional changes in patients' centering for use with a magnetic resonance imaging (MRI) machine. The kinematic imaging table is constructed of a non-magnetic material, so as not to interfere with the magnetic resonance imaging and may be motorized to allow automatic positional changes in patient centering under computer control during the diagnostic procedures. The diagnostic procedure entails the use of this table or other means to effect rapid positional changes, injection of an MRI contrast agent and the use of rapid imaging MRI sequences for the display of vascular territories along different anatomical positions of the body. According to another aspect of the present invention, a patient is injected with a contrast material, and multiple images are taken at different overlapping orientations using a single injection of an MRI contrast agent.

2. Background and Summary of the Invention

Various magnetic resonance angiography (MRA) techniques have been routinely employed in the past for imaging both arteries and veins in the body. The predominant techniques employed on a routine basis in clinical practice include 2D and 3D-time of flight (TOF), phase contrast and contrast-enhanced techniques. These techniques all have their advantages and are routinely employed to image specific target areas within the body. When imaging multiple target sites, however, all these techniques have their own inherent limitations. The clinical need for imaging multiple anatomic areas in the body is frequently encountered in practice, especially when evaluating the aorta. Patients with aortic dissection, require imaging of the thoracic and abdominal aorta. As such, two anatomical locations, specifically the chest and abdomen, need to be imaged. Patients with abdominal aortic disease and disease of the lower extremity arteries, require imaging of the abdomen, pelvis, thighs and legs down to and including the ankle region.

In conventional clinical practice, these territories are imaged with x-ray angiography following injection of iodinated contrast material directly into the aorta. Direct injection is via catheters that are placed within the aorta following arterial puncture and percutaneous placement of catheters, typically from the groin. These invasive techniques have a number of complications that are related not only to arterial puncture but also to the iodinated contrast that is administered. Complications such as thrombosis and occlusion of the femoral artery, pseudoaneurysm formation, bleeding and peripheral emboli are a few of the non-contrast related complications. Iodinated contrast complications include allergic reactions ranging from minor skin reactions to anaphylactic shock and death, and renal failure from contrast induced nephrotoxicity.

It is for these reasons, that MRI machines have been employed to image the arteries and veins using MRA techniques. 2D-time-of-flight techniques have been used to study the aorta and run-off circulation, however, even with the current state-of-the-art technology, multiple transverse slices are required with typical table times of 1.5 to 2 hours required for a complete examination covering the abdominal aorta to the ankle region. These techniques do not use intravenous contrast and image the blood vessels due to the inherent contrast of moving blood on gradient echo sequences due to the flow related enhancement phenomenon. Phase contrast techniques are likewise, time consuming. As such, breath-hold contrast enhanced techniques have been published in the literature, however, these have only been used in studying one anatomic region.

Currently, the FDA approved MRI contrast agents include gadopentetate dimeglumine (Magnevist, Berlex, Chicago, Ill.), gadoteridol (ProHance, Bracco Diagnostics, Princeton, N.J.) and gadodiamide (Omniscan, Nycomed). The first of these agents is an "ionic" agent and the latter of these two agents are "non-ionic" or net-0 charge agents with lower osmolality. The lower osmolality agents are approved for higher dose administrations. All of these agents are classified as extracellular agents that extravasate from the blood pool into the extracellular fluid space in a rapid manner. Pharmacokinetics have shown that 50% of the contrast dose that is injected into the peripheral vein of the upper extremity is cleared on first pass through the capillaries and 80% is cleared within five minutes. The route of elimination is via glomerular filtration through the kidneys. As such, rapid techniques are required to image the target arteries once the contrast is injected into the upper extremity vein. Likewise, one needs to appropriately time the data acquisition when the contrast arrives at the target site. Once the target site has been imaged, the data is processed yielding high resolution imaging of both arteries and veins. Veins are imaged by acquiring a delayed acquisition when venous return leads to the enhancement of the veins. Data subtraction of the arterial phase and venous phase data is performed to yield vein only images. The limitations of contrast-enhanced techniques for evaluating multiple anatomical locations, therefore, are primarily related to the current inability of any of the MRI machines available on the market in rapidly moving the patient table to image successive anatomical locations.

The details of an imaging table incorporating the use of surface coils is disclosed in our copending U.S. patent application, Ser. No. 08/766,289, entitled "Universal Kinematic Imaging Table for Rapid Positional Changes in Patient Centering," the disclosure of which is hereby incorporated by reference and summarized in the Detailed Description of the Preferred Embodiment presented below.

Therefore, it is desirable in the art of radiology to provide an imaging device which provides high resolution images and which permits rapid positional changes in patient centering so that the time required for obtaining accurate images of a patient may be reduced and so that movement of the patient relative to the imaging coils is simplified.

Accordingly, the present invention provides a magnetic resonance imaging device including an examination table movably supported on a track. A lower surface coil is supported under the table, and an upper surface coil is supported above the table. The table is movable relative to the upper and lower surface coils.

The present invention provides a procedure and apparatus which allows rapid positional change in the patient centering in order to facilitate the imaging of blood vessels in a series of different views, and to reduce the time required for obtaining the necessary images for a medical imaging examination using a single injection of an MRI contrast agent.

Further areas of applicability of the present invention will become apparent from the detailed description provided hereinafter. It should be understood however that the detailed description and specific examples, while indicating preferred embodiments of the invention, are intended for purposes of illustration only, since various changes and modifications within the spirit and scope of the invention will become apparent to those skilled in the art from this detailed description.

BRIEF DESCRIPTION OF THE DRAWINGS

The present invention will become more fully understood from the detailed description and the accompanying drawings, wherein:

FIG. 3 is a perspective view of a platform having a rolling track according to the principles of the present invention;

DETAILED DESCRIPTION OF THE PREFERRED EMBODIMENTS

Figure 1:
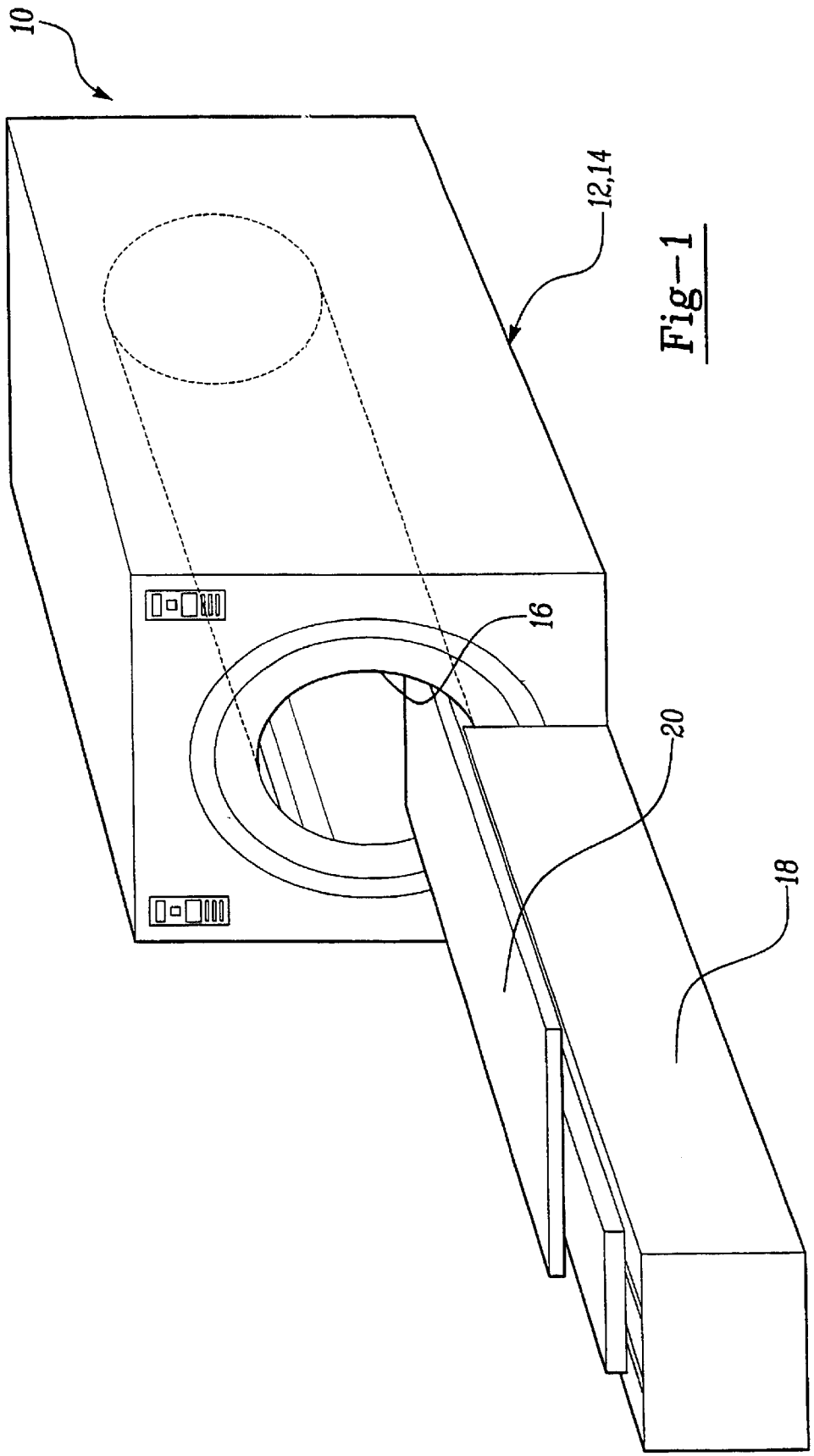
FIG. 1 is a general schematic view of a CT and MRI imaging device.

As shown in FIG. 1, the imaging device 10 generally includes a computed topography gantry 12 or a magnetic resonance imaging gantry 14. The computed tomography gantry and magnetic resonance imaging gantry each include a tunnel 16 for receiving a patient therein. A platform 18 is provided for supporting an examination table 20 which is received in the tunnel 16 of the imaging device 10.

According to the principles of the present invention, a kinematic imaging table is provided for rapid positional changes in patient centering. Existing MRI machines are provided with movable tables, however, these tables and their respective control systems are designed to lock the table in place during a scan sequence and do not permit the examination table to be moved without requiring the MRI device to be recalibrated after the examination table is moved. Furthermore, the existing CT or MRI machines are not capable of rapid positioning for patient centering in order to allow the patient to be repositioned for each scan sequence. Accordingly, existing CT and MRI machines can be retrofitted with a kinematic imaging table such as shown and described with respect to FIGS. 2–7.

Figure 2:
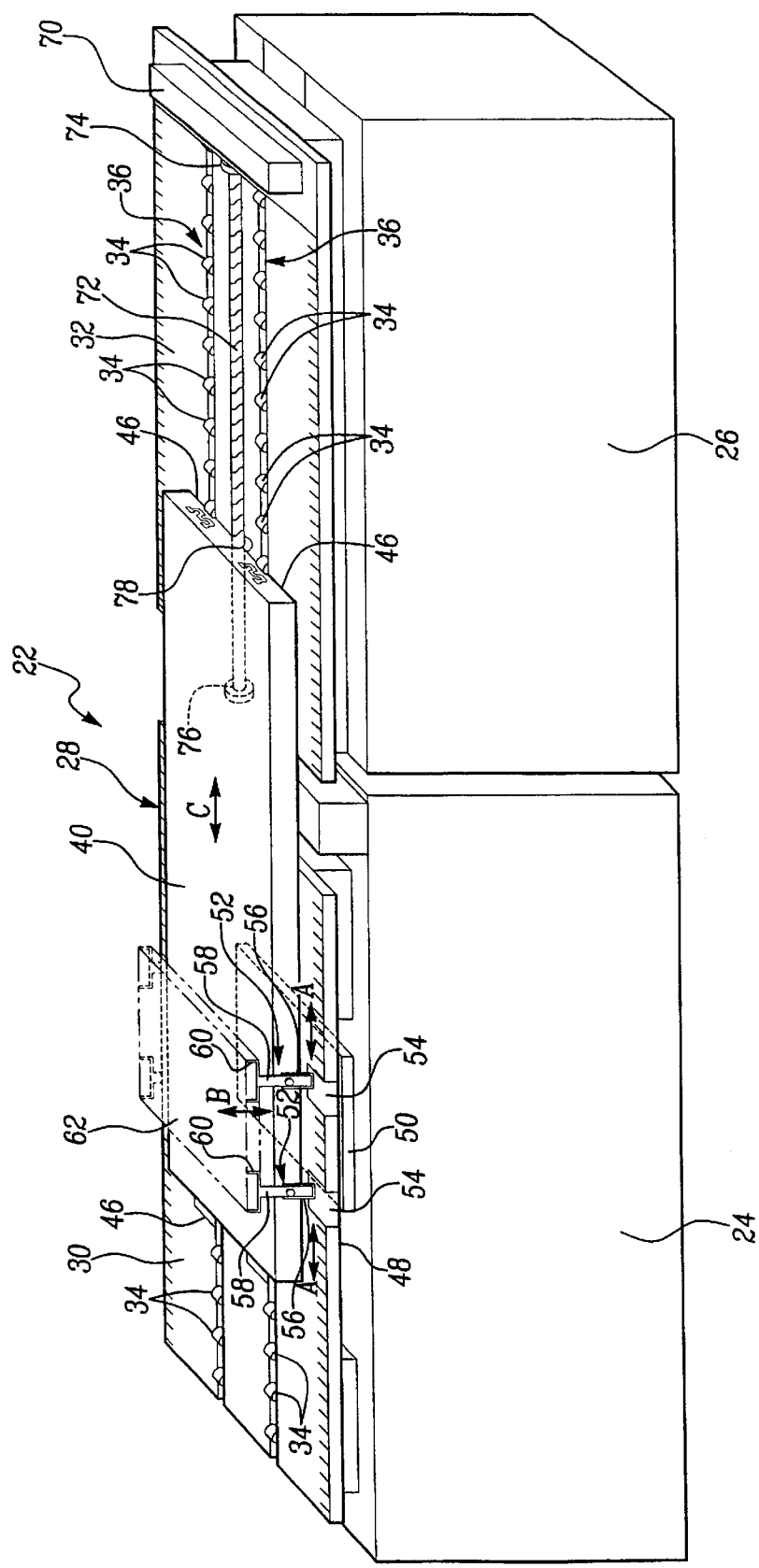
FIG. 2 is a perspective view of the universal kinematic imaging table suitable for use in performing the diagnostic procedures according to the principles of the present invention.
Figure 4:
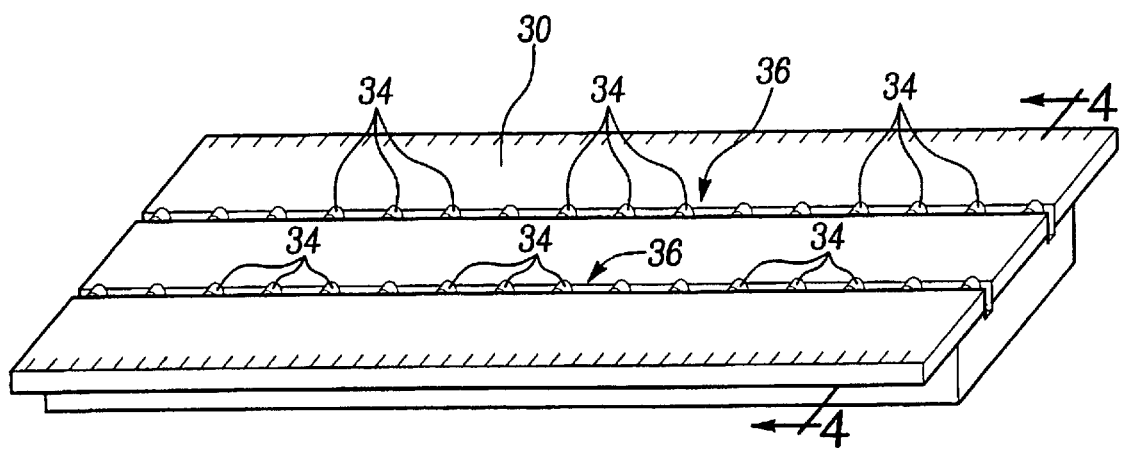
FIG. 4 is a sectional view taken along line 4—4 of FIG. 3.
Figure 4:
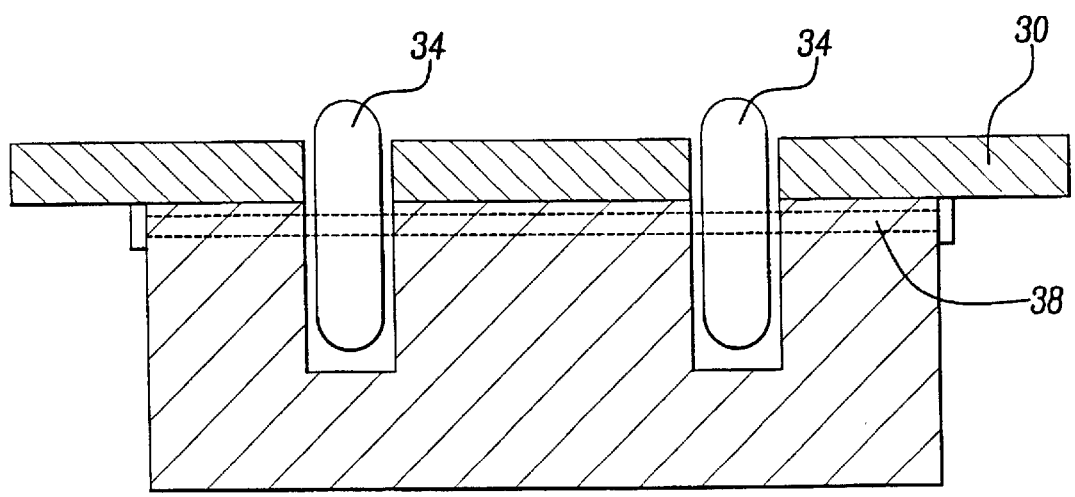
Figure 5:
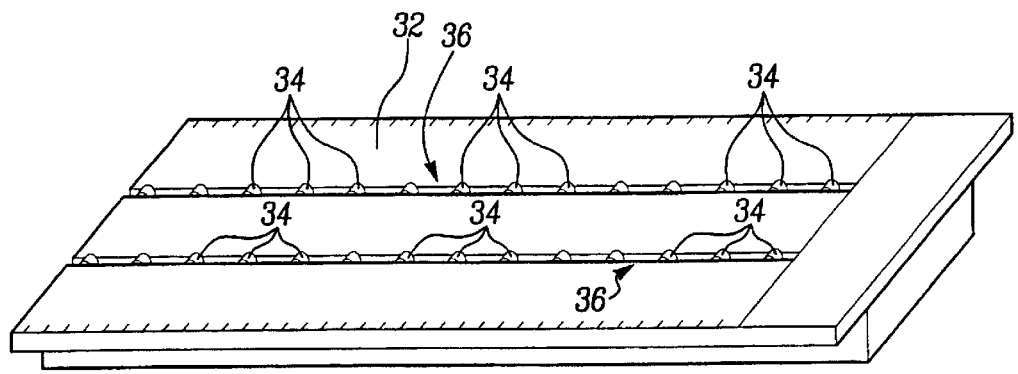
FIG. 5 is a perspective view of a second platform section having a rolling track disposed on an upper surface thereof.
Figure 6:
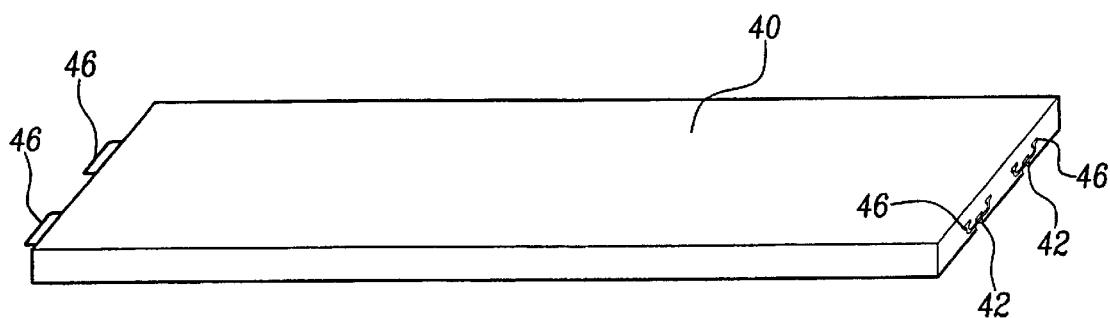
FIG. 6 is a perspective view of a movable table according to the principles of the present invention.
Figure 7:
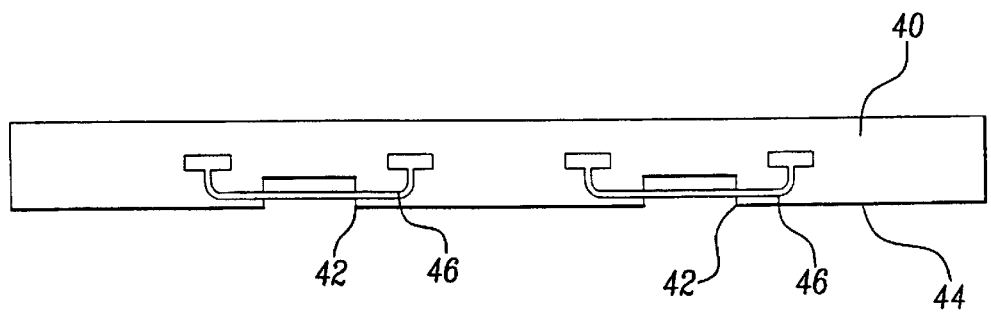
FIG. 7 is an end view of the movable table shown in FIG. 6.

With reference to FIG. 2, the imaging table 20 of the present invention is shown in combination with existing imaging and outer tables 24, 26, respectively. The kinematic imaging table 22 of the present invention includes a base platform 28 including a first platform portion 30 and a second platform portion 32. The first platform portion 30 is disposed on the existing imaging table 24. The second platform portion 32 is provided on the existing outer table 26. Outer table 26 may be provided with vertical adjustment capabilities for raising and lowering second platform portion 32. First and second platform portions 30, 32 are provided with a plurality of rollers 34 arranged in a pair of columns 36. Rollers 34 are supported by rods 38, as shown in FIG. 4. Rollers 34 and rods 38 are preferably made from a non-ferrous material such as plastic.

An examination table 40 is supported on the plurality of rollers 34. Examination table 40 is provided with grooves 42 extending longitudinally along a lower surface 44 thereof. Examination table 40 can be provided with handles 46 disposed on the ends or sides of the table 40. Examination table 40 is preferably made from a non-ferrous material such as plastic or wood.

An area beneath the first platform portion 30 is provided with an opening which defines a space 48 for receiving a lower or posterior surface coil 50 therein. The posterior surface coil 50 is provided in the form of a rectangular plate which contains the coils therein. A pair of movable support members 52 are disposed on each side of the first platform portion 30. The support members 52 include C-clamps 54 which attach to the platform 30 and are adjustable in the longitudinal direction as shown by arrows A. The support member 52 further includes a vertically-extending post 56 and an adjustable slide member 58 having a coil-supporting bracket 60 disposed at an upper portion thereof. The slide members are adjustable relative to posts 56 as shown by arrows B. An anterior or upper surface coil 62 is supported on the brackets 60 of support members 52. The upper surface coil 62 is disposed directly above lower surface coil 50.

In operation, the examination table 40 is disposed on the second platform portion 32 on outer table 26. A patient is placed on the examination table 40 and the table is rolled onto the first platform portion 30 and positioned such that the portion of the patient which is desired to be imaged is located between the upper and lower coils 62, 50. During the imaging process, the patient can be moved relative to the upper and lower coils 62, 50 by a technician who will use the handles 46 for moving the table. Alternatively, a motor 70 can be utilized for automatically adjusting the position of the examination table 40. Motor 70 is provided with a forward and reverse operating mode and has an output shaft attached to a screw device 72 which is supported by bearings 74, 76. Screw device 72 engages a nut 78 attached to examination table 40. The rotation of screw 72 causes nut 78 to travel along the axis of the screw 72, thereby moving the examination table 40 in the longitudinal direction as indicated by arrows C. Reversal of the motor 70 causes the screw device 72 to drive in the opposite direction, thereby causing the examination table 40 to move in the opposite direction.

In the invention disclosed above, the examination table 40 and rollers 34 may be placed wider apart so that the posterior coil can be placed directly beneath the examination table between the columns 36 of rollers 34. Furthermore, the rollers 34 may also be provided on the bottom of the examination table 40 while the first and second platform portions would then be provided with a track for receiving the rollers. It should be understood that other known track devices can be utilized for slidably supporting the examination table on the base platform.

The above described kinematic table provides a method of retrofitting existing MRI or CT machines to allow rapid positional changes of a patient so that a series of images can be taken of several portions of a patient's body using a single injection of contrast materials. However, it should be understood that MRI or CT machines can be designed to carry out the process of the present invention.

The kinematic imaging table of the present invention allows for the use of surface coils of an MRI machine for use in rapidly imaging different body locations in sequence including blood vessels and could therefore replace the predominant technique of x-ray angiography which is invasive, expensive and time consuming.

When performing MRA of different anatomical locations using a rapidly movable imaging table (perhaps of the type described above) and surface coils, FDA approved control materials can be injected into a peripheral vein, typically the upper extremity vein. As mentioned, the FDA approved agents include Magnevist, ProHance and Omniscan. Newer agents are also being tested in FDA clinical trials.

The most promising agent is a blood pool agent (MS 325, Epix Medical, Inc., Cambridge, Mass.). MS 325 is classified as a blood pool agent since it does not extravasate into the extracellular space. As such, it can be viewed as a more potent contrast enhancing agent when imaging blood vessels. Iron oxide particles when injected in a low dose, can also lead to contrast enhancement of blood vessels, and one of these agents is currently FDA approved but for imaging of the liver (Feromoxide). Computed tomography agents include omnipaque, renograffin and hypaque.

The dose of contrast and rate of injection of the contrast material varies among different contrast groups. Typically, the extracellular gadolinium chelates (Magnevist, Omniscan and ProHance) can provide adequate imaging of a target area with a dose of 0.1 mmol/kg and at a rate of 2–3 cc/sec.

With current MRI systems, when an anatomical location is completely imaged, the table and patient are then moved centering a different anatomical location in the center of the magnetic field. Using conventional techniques, this requires a considerable amount of time including moving the surface coils that are placed anterior and posterior to the body to be properly aligned with the different anatomical location as well as the center of the magnetic field. When ready to image the next anatomical location, additional contrast material will be required. Furthermore, baseline images will be essential to subtract the veins from the arteries. If there is motion of the patient in between the baseline and immediate post-contrast scans, there will be misregistration and inability to subtract the veins yielding suboptimal arterial phase images. As such, this will lead to patient discomfort and potentially, non-diagnostic images.

Using the kinematic imaging table according to the medical procedures of the present invention, when the imaging of one anatomical location is complete (imaging time with current MRA software requires approximately 15–25 seconds), the table can be moved in either a manual or automatic fashion to center the second anatomical location within the center of the magnetic field and relative to the anterior and posterior coils. In this fashion, the second anatomical location can be imaged during the arterial phase of contrast circulation, similar to what is done with an x-ray angiography stepping table and the use of x-ray or digital filming. Finally, a third, or even more anatomical locations, can also be imaged by moving the table and patient additional times. This will result in the ability to image several anatomical locations such as the abdomen, thighs and legs, which is required in evaluating patients with peripheral arterial disease. If desired, the entire process may be run under computer control, as described below.

This technique and procedure will be essential, especially in a future of managed care when more rapid imaging is required at a reduced cost to society.

Currently, the average hospital and professional fee for an x-ray aortogram with runoff evaluation is thirty five ($3500) hundred dollars. In comparison, the current average price for an MRI study employing one hour of table time is fifteen ($1500) hundred dollars. This price could also be lowered especially if imaging times are decreased with the current technology that is described herein. The cost should also decrease with newer contrast agents as described above. The blood pool agent, MS 325, can be administered at much lower doses. Likewise, the blood pool contrast agents have the potential in providing even higher signal-to-noise of the blood vessels, especially those that are much smaller in size as found in the most distal aspect of the lower extremities. When imaging different anatomical locations in sequence, however, one needs to alter various imaging parameters, specifically the center of data acquisition.

Software Control of Orientation and Centering of Data Acquisition in Real Time When imaging vascular territories in different anatomical locations, they may travel to different spatial locations (anterior, posterior, right or left). The volume of tissue that is typically imaged with the MRI machine, is typically defined to a certain dimension that is governed by the spatial resolution that is required and the imaging time that can be used to sufficiently image the vascular territory with sufficient spatial resolution and signal-to-noise. With a fixed volume of data acquisition, one will need to vary the position and, perhaps, the orientation of data acquisition when moving from one anatomical location to the other.

When imaging the chest and abdomen, the ideal orientation for imaging the thoracic aorta is typically an oblique sagittal projection, however, the abdominal aorta is typically evaluated in a frontal or coronal projection. As such, not only will the orientation of data acquisition change in moving from one location to the next, so will the center of data acquisition. When imaging the abdomen, thighs and legs in a typical run-off study, it is the frontal or coronal projection which is routinely employed, however, the center of data acquisition may change when moving from the abdomen to the ankle.

Software to change the orientation and centering of data acquisition over time, therefore, is highly desirable in the process of imaging different anatomical locations. Likewise, data calculation may be postponed until all of the anatomical locations have been imaged.

Figure 8:
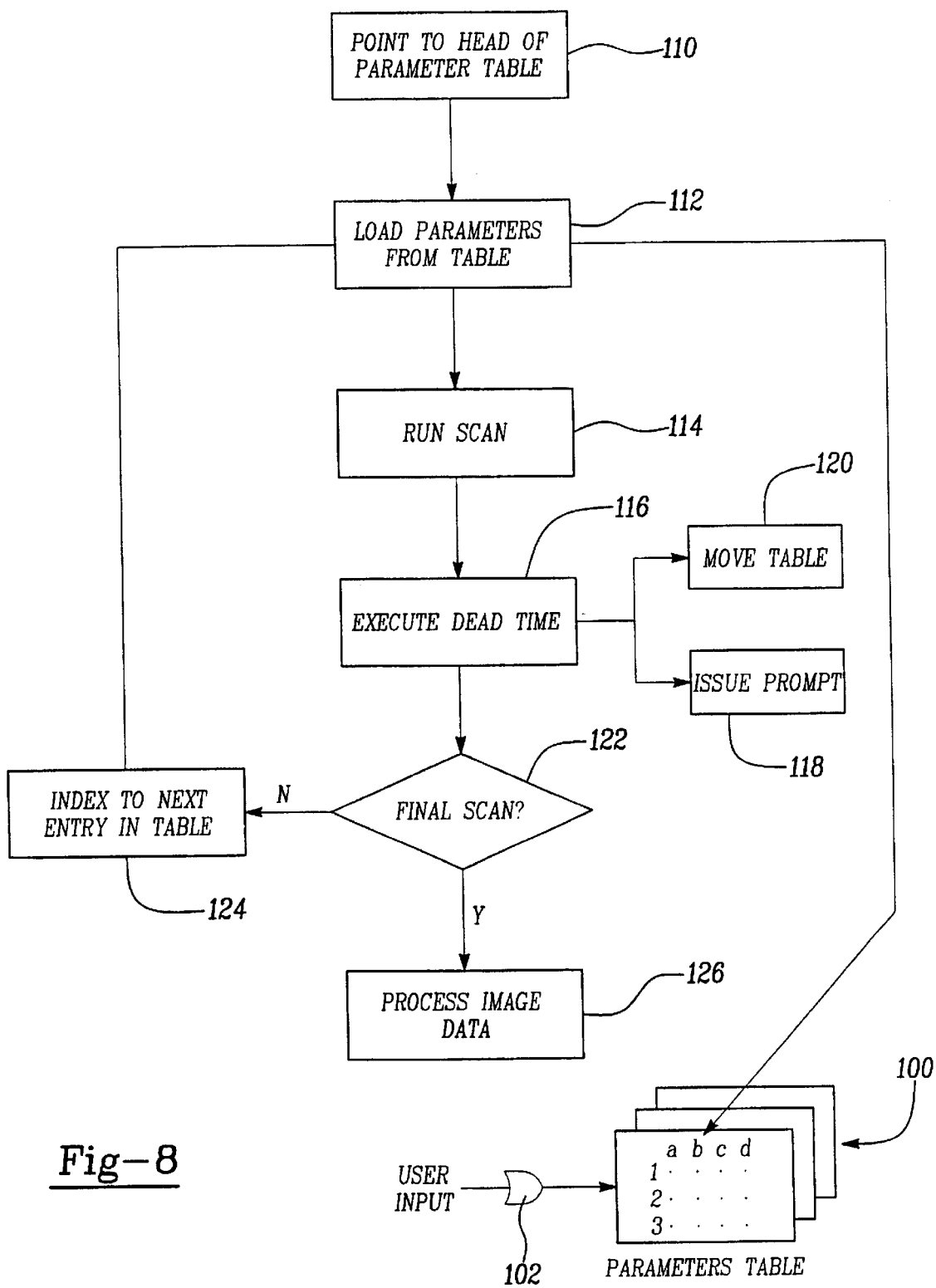
FIG. 8 is a software flowchart diagram describing how computer control of the diagnostic procedures may be implemented.
Figure 9:
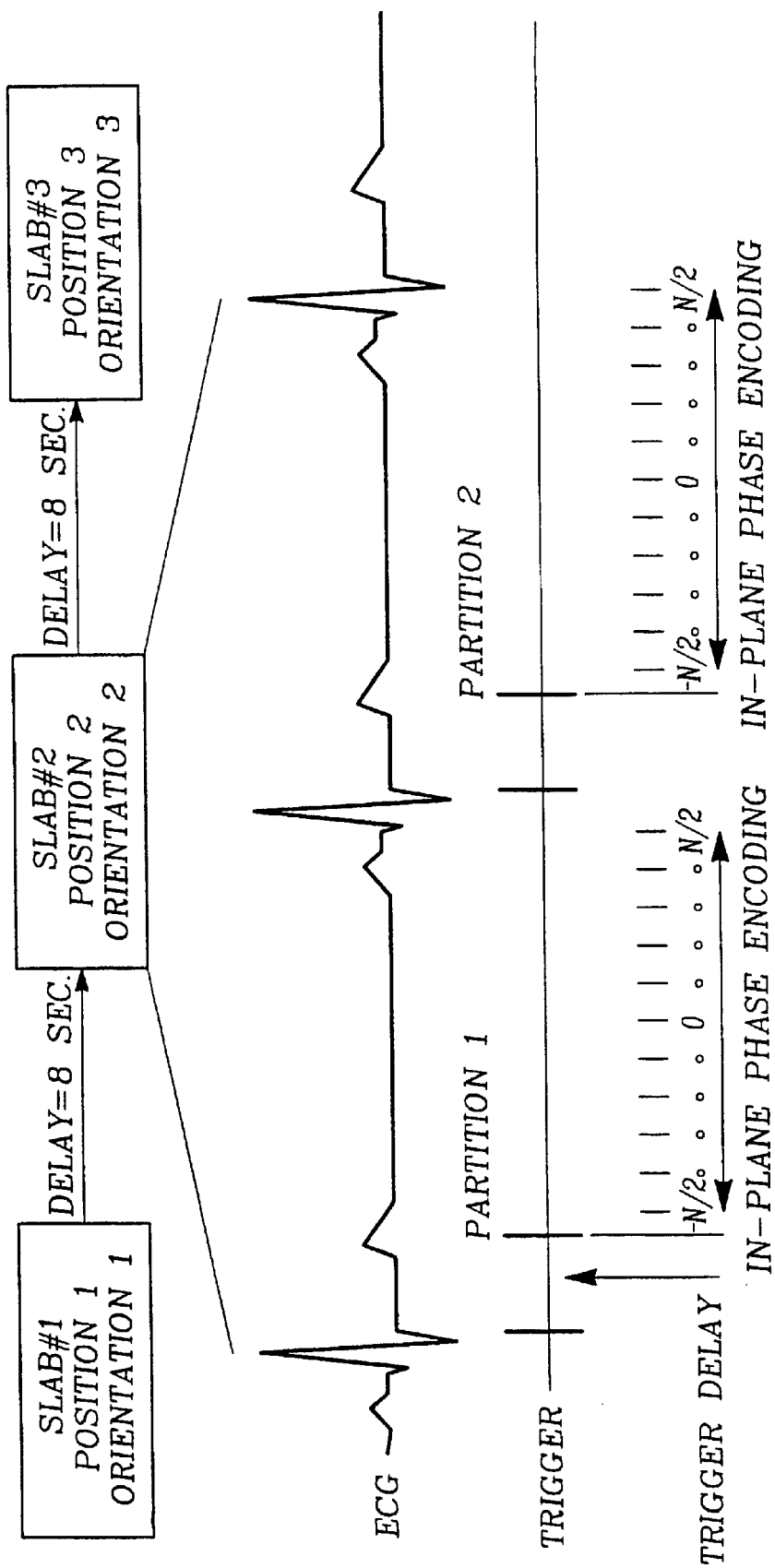
FIG. 9 provides a pulse sequence schematic showing the data acquisition procedure.

FIG. 8 shows how the software system of the improved data acquisition invention may be implemented. Although there are a number of different ways to achieve the data acquisition sequence, the illustrated embodiment uses a conditional branching loop to cycle through the plurality of views, selecting parameters from a parameter table. In FIG. 3, the parameter table is shown diagrammatically at 100. In the illustrated example, there are four parameters (a, b, c, d) for each of three views (1, 2, 3). The parameters may be supplied by user input through a suitable interface 102. If desired, multiple parameter tables can be stored in the system and used as templates for performing different types of MRI techniques. The user would then select the appropriate template corresponding to the type of procedure being performed, and would then enter into the template the desired parameters corresponding to the patient's physical characteristics or to the radiologist's instructions.

The software routing begins at Step 110 by pointing to the head of the parameter table. As will be described, the pointer is used to determine what parameters are loaded from the table. The pointer is indexed to the next set of parameters in the table of each of the views to be performed.

After initializing to the head of the parameter table, the routing, in Step 112, loads the parameters from the table into the system for execution. Then, in Step 114, after the patient has been injected with a suitable contrast material and the material has traveled through the arterial system to the body portion being viewed, the scan for the current view is run. This will involve acquiring all lines of data for all partitions that comprise the current view. After the scan for the current view is complete, the system then executes a dead time routine at 116. Preferably, the dead time interval can be a predetermined value supplied by the user through user interface 102. Although the current system uses the same dead time value between all views, the system can be readily adapted to execute different dead times between views, as may be desired in a particular procedure. Typically, the dead time will correspond to the amount of time it takes for a patient to exhale and inhale and again hold his or her breath for the next view to be taken at a different location or at a different orientation. Furthermore, when the patient is being moved so that a different body portion (such as moving from the abdomen to the legs) is being imaged, the dead time can correspond to the time it takes for the contrast material to travel from the first body portion being viewed to a second body portion to be viewed.

It will be recalled that during the dead time the patient is permitted to exhale and inhale. If desired, the system can be programmed to issue a prompt at Step 118 to notify the attending technician or patient that the patient may exhale and inhale. A suitable audible or visual prompt can be generated for this purpose. Also, if the system is configured to perform automatic patient repositioning, the appropriate motor control signals are generated to move the table on which the patient is resting at Step 120.

After the dead time is complete, the program tests at conditional branching operation 122 whether the final scan specified in the parameter tables has been completed. If not, control branches to Step 124, where the parameter tables pointer is indexed to the next entry in the table, and the program branches back to Step 112. At this time, additional images are obtained in sequence until the desired orientations and/or the desired portions of the body are imaged in series. If the final scan has been completed at Step 122, then control branches to Step 126, where the image data for all views are then processed.

The procedure described here also permits a dynamic contrast-enhanced 3D-breath-hold MRA technique using a multi-orientation and multiple overlapping thin slab acquisition (MO-MOTSA) with a single injection of contrast material.

Finally, regarding contrast administration, a fixed rate and volume of contrast followed by a fixed rate and volume of saline flush can be delivered with the use of automated power injectors that are available on the market today for MRI and MRA studies. The use of power injectors enhance the reproducibility of studies and more accurately deliver the contrast required for imaging of blood vessels. Prior to contrast administration, a small test dose (2 cc) of contrast is typically administered and rapid imaging is performed at the level of interest over time (typically 30–90 seconds). The time of contrast arrival is determined from this test and is subsequently used to determine the onset of data acquisition following the intravenous administration of the remaining contrast dose (10–40 cc).

Description of Clinical Examples

Three dimensional magnetic resonance angiography (3D-MRA) techniques have been routinely used in the past for vascular imaging. In particular, 3D-MRA in a single breath-hold [Simonetti OP, Finn J P, White R D, Bis K G, Shetty A N, et al. ECG-triggered breath-held gadolinium-enhanced 3D MRA of the thoracic vasculature(abstr). In: Book of abstract: International society of Magnetic Resonance in Medicine 1996:703. Shetty A N, Shirkhoda A, Bis K G, Alcantara A. Contrast enhanced three dimensional MR angiography in a single breath hold: A novel technique. AJR 1995;165:1290–1292.] has been shown to be a very useful and rapid technique when used with paramagnetic contrast agents. Given the rapid nature of this new sequence, with the acquisition of an entire 3D-data set during the passage of MR contrast material through the arterial system, arterial phase imaging is possible. A delayed acquisition following the initial arterial phase results in the visualization of venous flow. Conventionally, a breath-hold 3D-MRA study is performed by placing a single slab (view) of a desired thickness whose orientation is set to cover most of the vessels in question. The number of partitions within the slab (view) and in-plane phase encoding steps are adjusted to complete the acquisition in a reasonable single breath-hold period which is anywhere from 15–25 seconds. The data processing takes anywhere from 20–40 seconds depending on the data array size. These techniques have been successfully used to obtain a dynamic measurement in a single orientation. [Maki J H, Prince M R, Londy F, Chenevert T L. The effect of time varying intravascular signal intensity and k-space acquisition order on 3D MR angiography image quality (abstr). In: Book of abstract: International Society of Magnetic Resonance in Medicine 1996:237. Debatin J F, Schmidt M., Gohde S., Hany T., Pfamatter T, Krestin G P., McKinnon GC. 3D breath hold MRA of the renal arteries under 30 seconds. (abstr). In: Book of abstract: International Society of Magnetic Resonance in Medicine 1996:165.] In many cases, multiple measurements are made in the same orientation to obtain arterial and venous phase information. However, to obtain additional images at a different orientation, the data acquisition is repeated by repositioning the slab (view) with a new orientation. A different orientation is frequently required to better portray the 3-dimensional aspects of complex vascular anatomy with high resolution. Since, the data acquisition of the newly positioned slab (view) can only commence after the previous image data processing is completed, a wait of about 1–2 minutes between scans is elapsed during which most of the contrast bolus is washed out. A subsequent measurement will yield images with poor arterial and venous signal due to this prolonged delay. The present invention provides a method in which multiple slabs (views), either in the same or different orientation may be prescribed to acquire the arterial and venous phases with a single contrast injection.

Materials and Methods

All studies were performed using a 1.5 Tesla Magnetom Vision MR system (Siemens Medical Systems, Iselin, N.J.). Thirty subjects with known aortic (10thoracic, 1 abdominal, 1 arch vessel), pulmonary artery (6), or cardiac (7) disease and 5 volunteers were recruited with informed consent approved by the institutional review board of the hospital. Patients were positioned supine with a quadrature phased array body coil. A 20-gauge angio-cath needle was placed in an anticubittal vein and the other end of the line was connected to a contrast injector (Spectra II, MedRad, Pittsburgh, Pa.) which was used to infuse contrast at a rate of 2 or 3 cc /sec. Any 3D MRA or MRI pulse sequence can be used with this technique. We used an ECG triggered 3D FLASH (Fast Low Angle single Shot) pulse sequence. Each of the partitions along the slab (view) select direction was acquired by triggering at the R-wave. Thus, the number of partitions correspond to the number of heart beats. About 96 lines were acquired in a single R—R interval for each partition. The number of lines that were acquired depended on the patient's R—R interval and the time to complete a single line of data acquisition. The imaging parameters were TRITE=5.0/2.0, flip angle=15°, matrix=96×256, partition thickness=2–3 mm and the number of partitions were limited to 22–30 so that a single measurement could be completed in a reasonable single breath hold (after deep inspiration) period. It should be noted that the above sequence is just one sequence that was implemented. Other gradient echo, spin echo or fast (turbo) spin echo sequences can also be implemented using this concept.

The delay between successive slab measurements was fixed at 8 seconds. During this period patients were prepared to hold their breath for the next measurement. Prior to contrast injection, the sequence was applied once to obtain base-line images in the same three orientations which were then used for subtracting from the corresponding post-contrast images. Subtraction was used in only 5 patients where as in remaining patients source images resulting from contrast were used. Prohance (Gadoteridol) (Bracco Diagnostics, Princeton, N.J.) at the dose of 0.2 mmol/kg was injected at the rate of 2 or 3 cc/sec using the injector followed by 15 cc of saline flush. The first measurement was obtained between 5–10 seconds(for pulmonary studies) or 10–15 seconds (for aortic studies) after the onset of contrast injection. Second and third measurements were subsequently obtained with a total time for all three measurements of 54 seconds.

Results

All patients tolerated three successive measurements with breath-holding. All measurements revealed a moderate enhancement of the blood pool of the target area of interest. All 30 subjects underwent 3 measurements in which 26 were imaged in two different planes (one of the imaging plane was repeated) over time and four were imaged with three different planes over time. Among the 10 patients with thoracic aortic disease, the following abnormalities were imaged: Type A dissections (4), Type B dissections (2), aorto-annular ectasia (1), atherosclerotic aneurysms (2) and atherosclerotic narrowing (1). There were two normal thoracic aortas imaged. One plane of imaging is not optimum in dissection patients since the imaging plane may be parallel with the intimal flap which may go undetected. The three-dimensional relationships of thoracic aortic aneurysms was also better appreciated with the MO-MOTSA technique.

Among the pulmonary abnormalities, the following were imaged with MOMOTSA: pulmonary artery aneurysm (1), lung carcinoma mimicking arteriovenous malformation on CT (1), infiltrate/atelectasis (2) and chronic pulmonary embolus (1).

There were seven patients with a variety of cardiac abnormalities that were imaged with MO-MOTSA and included the following: hydatid cyst of the interventricular septum (1), pericardial effusions (3), pericardial cyst (1), right atrial lipoma (1) and left ventricular aneurysm with thrombus (1). Thickening of the pericardium with pericardial effusions was better appreciated with the multi-planar aspects of MO-MOTSA imaging.

Discussion

We have shown a new way of acquiring 3D-MRA images in multiple orientations. The technique can also be used in other parts of the body for depicting vascular and non-vascular anatomy. Typically, a 3D pulse sequence takes 15–18 seconds to complete 96 line and 24 partitions. By running the pulse sequence repeatedly, arterial and delayed arterial and venous phase imaging is possible. It should be noted that other sequences can also be implemented. Most scanners provide a means to achieve this by increasing the number of measurements of the same slab orientation with an appropriate time delay between measurements. However, this restricts one to achieving vascular information along only one orientation. To render projections along the other directions, a multi-planar reformatting (MPR) of the data can be used before subjecting the data to maximum intensity projection (MIP), however, the spatial resolution is lost especially when the raw data voxels are non-isotropic. In addition, with MIP, due to pixel replication, the projections deviating significantly from the true acquisition plane have a significantly diminished resolution. The method described here allows for acquiring data in multiple orientations without a loss of vascular signal. This also allows for MIP along those multi-planar directions without the loss of spatial resolution.

Using a variable delay between 3D slabs allowed for imaging of vascular territories in different orientations during the arterial peak of contrast enhancement. The method is very useful in obtaining high resolution images of the aorta and pulmonary vasculature and cardiac anatomy. This method may also prove useful in the future when the patient table is moved to center different anatomic locations in the center of the magnet when performing aortic runoff evaluations or when the need for imaging the thoracic and abdominal aorta arises.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A diagnostic procedure using a magnetic resonance imaging device, comprising the steps of:

laying a patient on a movable table and positioning said patient in a first position relative to said magnetic resonance imaging machine;

injecting said patient with a contrast material;

performing a first scan sequence of a first body portion with said magnetic resonance imaging machine;

moving said patient to a second position relative to said magnetic resonance imaging machine; and performing a second scan sequence of a second body portion with said magnetic resonance imaging machine within a predetermined amount of time corresponding to travel of said contrast material from said first body portion to said second body portion.

2. The diagnostic procedure according to claim 1, wherein said contrast material is selected from a group consisting of gadopentetate dimeglumine, gadoteridol, and gadodiamide.

3. The diagnostic procedure according to claim 1, wherein said magnetic resonance imaging machine includes a surface coil disposed under said movable table and a surface coil disposed over said table, said movable table being movable relative to said surface coils.

4. The diagnostic procedure according to claim 3, wherein said surface coil disposed under said movable table does not move relative to magnetic resonance imaging machine from said performing a first scan sequence to said performing said second scan sequence.

5. The diagnostic procedure according to claim 4, wherein said surface coil disposed over said movable table does not move relative to magnetic resonance imaging machine from said performing a first scan sequence to said performing said second scan sequence.

6. The diagnostic procedure according to claim 3, wherein said surface coil disposed over said movable table does not move relative to magnetic resonance imaging machine from said performing a first scan sequence to said performing said second scan sequence.

7. A diagnostic procedure using a computed tomography machine, comprising the steps of:

laying a patient on a movable table and positioning said patient in a first position relative to said computed tomography machine;

injecting said patient with a contrast material;

performing a first scan sequence of a first body portion with said computed tomography machine;

moving said patient to a second position relative to said computed tomography machine; and performing a second scan sequence of a second body portion with said computed tomography machine within a predetermined amount of time corresponding to travel of said contrast material from said first body portion to said second body portion.

8. The diagnostic procedure according to claim 7, wherein said contrast material is selected from a group consisting of omnipaque, renograffin and hypaque.

9. A diagnostic procedure using a magnetic resonance imaging device, comprising the steps of:

positioning a patient in a magnetic resonance imaging machine;

injecting said patient with a contrast material;

performing a first scan sequence with said magnetic resonance imaging machine to obtain a first image of a body portion; and performing a second scan sequence with said magnetic resonance imaging machine to obtain a second image of said body portion at a different orientation from said first scan sequence;

wherein a delay period is provided between said steps of performing said first scan sequence and performing said second scan sequence, said delay period being long enough to allow a patient to breath between said first and second scan sequences but within an amount of time for said contrast material to pass from said body portion.

10. The diagnostic procedure according to claim 9, wherein said contrast material is selected from a group consisting of gadopentetate dimeglumine, gadoteridol, and gadodiamide.

* * * * *